United States Patent [19]

Grohe et al.

[11] Patent Number: 4,808,583
[45] Date of Patent: Feb. 28, 1989

[54] SOLUTIONS OF LACTIC ACID SALTS OF PIPERAZINYLQUINOLONE- AND PIPERAZINYL-AZAQUINOLONE-CARBOXYLIC ACIDS

[75] Inventors: Klaus Grohe, Odenthal; Robert Lammens, Leverkusen, both of Fed. Rep. of Germany

[73] Assignee: Bayer Aktiengesellschaft, Leverkusen, Fed. Rep. of Germany

[21] Appl. No.: 71,459

[22] Filed: Jul. 9, 1987

Related U.S. Application Data

[62] Division of Ser. No. 862,343, May 12, 1986, which is a division of Ser. No. 644,834, Aug. 27, 1984, Pat. No. 4,705,789.

[30] Foreign Application Priority Data

Sep. 17, 1983 [DE] Fed. Rep. of Germany ....... 3333719

[51] Int. Cl.$^4$ .................... A61K 31/50; A61K 31/495
[52] U.S. Cl. .................................... 514/254; 514/970
[58] Field of Search ....................... 514/233, 970, 254

[56] References Cited

U.S. PATENT DOCUMENTS 4,022,894  5/1977  Fainberg et al. ................ 514/223.2

FOREIGN PATENT DOCUMENTS 0009425  4/1980  European Pat. Off. ............ 514/254
0047005  3/1982  European Pat. Off. ............ 514/227
0067666  12/1982  European Pat. Off. .
3037103  5/1981  Fed. Rep. of Germany ...... 514/254
0188515  11/1982  Japan ................................. 514/970

*Primary Examiner*—Allen J. Robinson
*Attorney, Agent, or Firm*—Sprung Horn Kramer & Woods

[57] ABSTRACT

The invention relates to solutions of piperazinylquinolone- and piperazinyl-azaquinolone-carboxylic acids, and in particular both ready-to-use injection and/or infusion solutions and dosage forms which can be converted into such injection and/or infusion solutions before use. The solutions according to the invention are characterized in that, besides the lactic acid salts of the active substance and, if appropriate, customary auxiliaries, they additionally contain at least one acid which does not lead to precipitates, in particular lactic acid.

6 Claims, No Drawings

SOLUTIONS OF LACTIC ACID SALTS OF PIPERAZINYLQUINOLONE- AND PIPERAZINYL-AZAQUINOLONE-CARBOXYLIC ACIDS

This is a division of application Ser. No. 862,343, filed 5-12-86, now pending, which is a division of Ser. No. 644,834, filed 8-27-84, now U.S. Pat. No. 4,705,789.

The invention relates to solutions of piperazinylquinolone- and piperazinyl-azaquinolone-carboxylic acids, and in particular both ready-to-use injection and-/or infusion solutions and dosage forms which can be converted into such injection and/or infusion solutions before use.

The solutions according to the invention are characterised in that, besides the lactic acid salts of the active substance and, if appropriate, customary auxiliaries, they additionally contain at least one acid which does not lead to precipitates, in particular lactic acid.

Possible active substances are at least one of the compounds of the formulae I or II

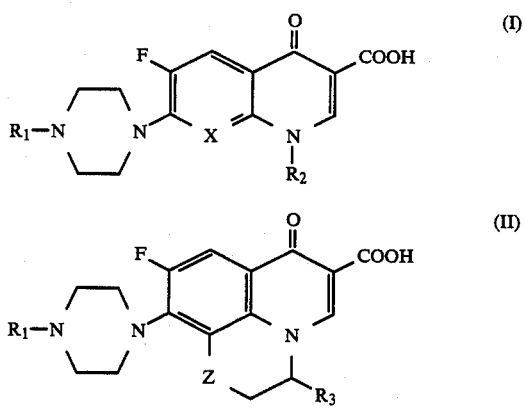

in which
X denotes N, C—H or C—F,
Z denotes O or $CH_2$,
$R_1$ denotes hydrogen methyl, ethyl or β-hydroxyethyl,
$R_2$ denotes cyclopropyl or ethyl and
$R_3$ denotes hydrogen, methyl or ethyl.

Compounds which may be mentioned in particular are: 1-cyclopropyl-6-fluoro-1,4-dihydro-4-oxo-7-(1-piperazinyl)-quinoline-3-carboxylic acid (compound A); 1-ethyl-6-fluoro-1,4-dihydro-4-oxo-7-(1-piperazinyl)-quinoline-3-carboxylic acid (compound B); 9-fluoro-3-methyl-10-(4-methyl-1-piperazinyl)-7-oxo-2,3-dihydro-7H-pyrido[1,2,3-de]-1,4-benzoxazine-6-carboxylic acid (compound C); 1-ethyl-6-fluoro-1,4-dihydro-4-oxo-7-(1-piperazinyl)-1,8-naphthyridine-3-carboxylic acid (compound D); and 1,cyclopropyl-6-fluoro-1,4-dihydro-4-oxo-7-(4-ethyl-1-piperazinyl)-quinoline-3-carboxylic acid (Compound E).

These substances are known to have powerful antibacterial action and are therefore suitable as medicaments for combating bacterial infections in warm-blooded animals.

The compounds of the formula I are known from: J. Med. Chem. 23 1958 (1980); DE-OS (German Published Specification) No. 3,142,854; DE-OS (German Published Specification) No. 3,033,157; and EP-OS (European Published Specification) No. 0,067,666.

The compounds of the formula II are known from: EP OS (European Published Specification) No. 0,047,005; DE-OS No. (German Published Specification) 3,037,103; and DE-OS No. (German Published Specification) 2,914,258.

Suitable customary auxiliaries for the solutions according to the invention are non-toxic, pharmaceutical carrier substances. These are, for example, thickeners, absorption accelerators, absorption inhibitors, crystallisation retarders, complexing agents, antioxidants, isotonicity agents or euhydrating agents. They can be solid, semisolid or liquid in consistency.

Examples of possible acids which do not lead to precipitates are methanesulphonic acid, propionic acid, succinic acid, hydrochloric acid and, in particular, lactic acid.

For various reasons, acid addition salts or alkali metal salts of active compounds are frequently used in pharmacy. Addition salts of the active substances can be prepared from several inorganic and organic acids, such as, for example, sulphuric acid, nitric acid, hydrochloric acid, citric acid, acetic acid, malic acid, succinic acid, tartaric acid, fumaric acid and methanesulphonic acid.

However, many such salts are unsuitable or very poorly suitable for the preparation of infusion and/or injection solutions, because, for example, the pH and/or the solubility and/or the shelf life, especially in respect of deposits, of the ready-to-use infusion and/or injection solution does not fulfil the pharmaceutical requirements to be imposed on such solutions.

It has now been found that the solutions can be stored if, besides the lactic acid salt of at least one of the active substances and, if appropriate, customary auxiliaries, they additionally contain at least one acid which does not lead to precipitates, in particular lactic acid.

The presence of such acids, in particular lactic acid, or, depending on the pH, a mixture of acid(s) and anion(s) thereof, is essential for the stability of the solution to be administered, in particular in respect of deposits.

Depending on the primary means of packaging used, the concentration of the active substance in the solution, the pH of the solution and the shelf-life requirements imposed, the content of excess lactic acid of the solutions according to the invention can be 0.01 to 90%. The lactic acid content of the solution to be administered can be 0.01 to 25% preferably 0.025 to 1.4%.

These quantity data relate to the total amount of excess acid, that is to say non-dissociated and dissociated acid.

Where these acids required for the stability are referred to below, in particular lactic acid, the total amount of excess acid is meant that is to say non-diisociated and dissociated acid.

If other acids which do not lead to precipitates are used, such as, for example, methanesulphonic acid, propionic acid, hydrochloric acid or succinic acid, the content of excess acid can be 0.05 to 4%, preferably between 0.3 and 2%, depending on the concentration of the active substance, the shelf-life requirements imposed and the pH of the ready-to-use solutions according to the invention.

The pH of the ready-to-use solutions according to the invention can be between 2.5 and 7, preferably between 3.5 and 4.5.

It was very surprising to discover that by addition of at least one acid which does not lead to precipitates, in particular lactic acid, in amounts such as those given above, it was also possible to stabilise infusion and/or injection solutions of the lactic acid salt of compound B, D and E, whilst the 1:1 stoichiometric salts of these compounds tended to give deposits. This also applies to the formulations, according to the invention, of compound C.

It has furthermore been found that there are several possible processes for the preparation of the solutions according to the invention.

The lactic acid salt of the active substance or a hydrate thereof can be used as the starting substance for the preparation of the solution of the active substance. In this case, it is possible to incorporate the required addition, or some of this addition, of at least one acid which does not lead to precipitates, in particular lactic acid, into the lactic acid salt, for example by freeze-drying.

However, the lactic acid salts can also be prepared directly in the solution, and in particular by addition of the amounts of lactic acid required for salt formation.

It is in this way possible to prepare both ready-to-use solutions of the active substance, filled in suitable containers, for example in ampoules or injection or infusion bottles, as well as precursors, for example concentrates or ampoules, suitable for the preparation of such solutions.

The solutions according to the invention, like the compounds of the formulae I and II on which they are based, are to be used as medicaments for combating bacterial infections. Possible uses are as injections and infusions. The dosages correspond to those of the known compounds A, B, C, D and E. Unless otherwise specified, all parts and/or percentages as used herein are parts or percentages by weight per unit volume.

FORMULATIONS

The solutions according to the invention are prepared by dissolving the active substance or the lactic acid salt thereof and, if appropriate, customary auxiliaries, in a solution of lactic acid or a mixture of lactic acid and, for example, sodium lactate, if necessary with slight warming.

If appropriate, water or a mixture of water and sodium hydroxide solution is also added to adjust the desired concentration of the active substance and/or the pH of the solution.

EXAMPLE 1

| | |
|---|---|
| 1-Cyclopropyl-6-fluoro-1,4-dihydro-4-oxo-7-(1-piperazinyl)-quinolone-3-carboxylic acid (compound A) | 150 g |
| Lactic acid (90% by weight) | 262 g |
| 2 M sodium hydroxide solution | 266 g |
| Water | to 15.0 liters |

EXAMPLE 2

| | |
|---|---|
| Monolactate of compound A | 1.27 g |
| Lactic acid (90% by weight) | 1.45 g |
| 2 M sodium hydroxide solution | 1.80 g |
| Mannitol | 1.37 g |
| Water | to 100.0 ml |

EXAMPLE 3

| | |
|---|---|
| Compound A | 10.00 g |
| Lactic acid (90% by weight) | 4.85 g |
| Water | to 1000.0 ml |

EXAMPLE 4

| | |
|---|---|
| 1-Ethyl-6-fluoro-1,4-dihydro-4-oxo-7-(1-piperazinyl)-quinolone-3-carboxylic acid (compound B) | 1.00 g |
| Lactic acid (90% by weight) | 0.50 g |
| Glucose | 3.85 g |
| Water | to 100.00 ml |

EXAMPLE 5

| | |
|---|---|
| 9-Fluoro-3-methyl-10-(4-methyl-1-piperazinyl)-7-oxo-2,3-dihydro-7H-pyrido-[1,2,3-de]-4-benzoxazine-6-carboxylic acid (compound C) | 5.00 g |
| Lactic acid (90% by weight) | 2.20 g |
| Water | to 100.00 ml |

EXAMPLE 6

| | |
|---|---|
| Dihydrate of the monolactate of compound A | 69.0 g |
| Lactic acid (90% by weight) | 24.2 g |
| Water | to 1000.0 ml |

EXAMPLE 7

| | |
|---|---|
| Compound A | 300.0 g |
| Lactic acid (90% by weight) | 177.3 g |
| Water | to 6000.0 ml |

EXAMPLE 8

| | |
|---|---|
| Compound A | 200.0 g |
| Lactic acid (90% by weight) | 75.0 g |
| Water | to 2000.0 ml |

EXAMPLE 9

| | |
|---|---|
| Monolactate of compound B | 128.2 g |
| Lactic acid (90% by weight) | 50.0 g |
| Water | to 1000.0 ml |

EXAMPLE 10

| | |
|---|---|
| Compound C | 100.0 g |
| Lactic acid (90% by weight) | 44.4 g |
| Water | to 1000.0 ml |

EXAMPLE 11

| | |
|---|---|
| Compound A | 30.0 g |
| Lactic acid (90% by weight) | to 100.0 g |

EXAMPLE 12

| | |
|---|---|
| Compound A | 1.00 g |
| Lactic acid (90% by weight) | 0.30 g |
| Succinic acid | 0.71 g |
| Water | to 100.00 ml |

Adjusted to pH 3.6 with 2 M sodium hydroxide solution.

EXAMPLE 13

| | |
|---|---|
| Monolactate of compound A | 1.27 g |
| Methanesulphonic acid | 0.60 g |
| Water | to 100.00 ml |

Adjusted to pH 3.9 with 2 M sodium hydroxide solution.

EXAMPLE 14

| | |
|---|---|
| Monolactate of compound A | 1.27 g |
| Lactic acid (90% by weight) | 0.56 g |
| Methanesulphonic acid | 1.45 g |
| Water | to 100.00 ml |

Adjusted to pH 3.7 with 2 M sodium hydroxide solution.

EXAMPLE 15

| | |
|---|---|
| Compound A | 1.00 g |
| Lactic acid (90% by weight) | 0.86 g |
| Propionic acid | 1.12 g |
| Water | to 100.00 ml |

Adjusted to pH 3.8 with 2 M sodium hydroxide solution.

EXAMPLE 16

| | |
|---|---|
| Compound B | 1.00 g |
| Lactic acid (90% by weight) | 0.87 g |
| Propionic acid | 0.46 g |
| Water | to 100.00 ml |

EXAMPLE 17

| | |
|---|---|
| Monolactate of compound B | 1.28 g |
| Lactic acid (90% by weight) | 1.11 g |
| Succinic acid | 1.85 g |
| Water | to 100.00 ml |

Adjusted to pH 3.7 with 2 M sodium hydroxide solution.

EXAMPLE 18

| | |
|---|---|
| Compound B | 1.00 g |
| Lactic acid (90% by weight) | 0.42 g |
| Methanesulphonic acid | 1.50 g |
| Water | to 100.00 ml |

Adjusted to pH 3.8 with 2 M sodium hydroxide solution.

EXAMPLE 19

| | |
|---|---|
| Compound C | 1.00 g |
| Lactic acid (90% by weight) | 0.39 g |
| Methanesulphonic acid | 0.53 g |
| Water | to 100.00 ml |

Adjusted to pH 3.9 with 2 M sodium hydroxide solution.

EXAMPLE 20

| | |
|---|---|
| Monolactate of compound C | 1.25 g |
| Lactic acid (90% by weight) | 0.56 g |
| Propionic acid | 1.03 g |
| Water | to 100.00 ml |

EXAMPLE 21

| | |
|---|---|
| Compound C | 1.00 g |
| Lactic acid (90% by weight) | 1.39 g |
| Succinic acid | 0.64 g |
| Water | to 100.00 ml |

Adjusted to pH 3.7 with 2 M sodium hydroxide solution.

EXAMPLE 22

| | |
|---|---|
| Compound A | 1.00 g |
| Lactic acid (90% by weight) | 0.33 g |
| 1 M hydrochloric acid | 1.20 g |
| Water | to 100.00 ml |

EXAMPLE 23

| | |
|---|---|
| Compound A | 1.00 g |
| Lactic acid (90% by weight) | 0.41 g |
| Water | to 100.00 ml |

Adjusted to pH 4.0 with 1 M hydrochloric acid.

EXAMPLE 24

| | |
|---|---|
| Compound A | 20.00 g |
| Lactic acid (90% by weight) | 8.26 g |
| Water | to 100.00 ml |

Adjusted to pH 3.6 with 1 M hydrochloric acid.

EXAMPLE 25

| | |
|---|---|
| Compound E | 1.00 g |
| Lactic acid (90% by weight) | 0.33 g |
| Water | to 100.00 ml |

EXAMPLE 26

| | |
|---|---|
| Compound E | 1.00 g |
| Lactic acid (90% by weight) | 0.44 g |
| Benzylalcohol | 1.00 g |
| Water | to 100.00 m. |

EXAMPLE 27

| | |
|---|---|
| Compound E | 1.00 g |
| Lactic acid (90% by weight) | 0.33 g |
| 1 M hydrochloric acid | 0.66 g |

-continued

| Water | to 100.00 ml |
|---|---|

EXAMPLE 28

| Compound E | 2.50 g |
|---|---|
| Lactic acid (90% by weight) | 0.83 g |
| 1 M hydrochloric acid | 1.65 g |
| Water | to 100.00 ml |

EXAMPLE 29

| Compound E | 10.00 g |
|---|---|
| Lactic acid (90 by weight) | 8.33 g |
| Hydrochloric acid (25%) | 1.30 g |
| Water | to 100.00 ml |

EXAMPLE 30

| Compound E | 5.00 g |
|---|---|
| Lactic acid (90% by weight) | 2.22 g |
| Sodiummetabisulfite | 0.20 g |
| Water | to 100.00 ml |

What is claimed is:

1. An aqueous storage stable solution which can be converted into an injection or diffusion solution consisting essentially of (a) a lactic acid salt of a piperazinyl-quinolone- or piperazinyl-azaquinolone-carboxylic acid of the formula

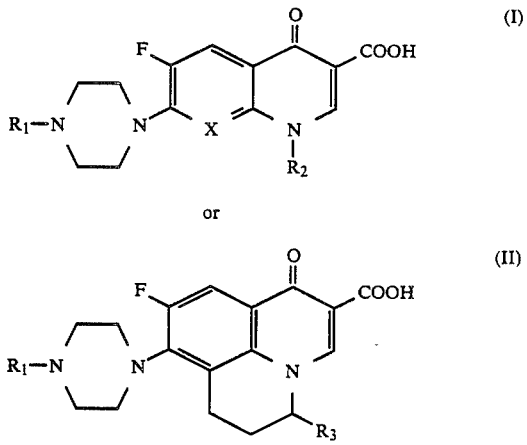

in which

X denotes N, C—H or C—F, $R_1$ denotes hydrogen, methyl, ethyl or β-hydroxyethyl, $R_2$ denotes cyclopropyl or ethyl and $R_3$ denotes hydrogen, methyl or ethyl, and (b) and excess acid selected from the group consisting of methanesulphonic acid, propionic acid, succinic acid and hydrochloric acid, the excess acid being present in an amount which does not lead to precipitates and constituting about 0.01 to 90% based on the solution.

2. A solution according to claim 1, which contains the lactate of 1-cyclopropyl-6-fluoro-1,4-dihydro-4-oxo-7-(1-piperazinyl)-quinoline-3-carboxylic acid.

3. A solution according to claim 1, which contains the lactate of 1-ethyl-6-fluoro-1,4-dihydro-4-oxo-7-(1-piperazinyl)-quinoline-3-carboxylic acid.

4. A solution according to claim 1, which contains the lactate of 1-ethyl-6-fluoro-1,4-dihydro-4-oxo-7-(1-piperazinyl)-1,8-naphthyridine-3-carboxylic acid.

5. A solution according to claim 1 in which the content of excess acid is 0.01 to 25%.

6. A solution according to claim 1, in which the content of excess acid is 0.025 to 1.4%.

* * * * *